(12) United States Patent
Plucienniczak et al.

(10) Patent No.: US 8,628,954 B2
(45) Date of Patent: Jan. 14, 2014

(54) EXPRESSION CASSETTE, USE OF THE EXPRESSION CASSETTE, VECTOR, HOST CELL, A METHOD FOR PRODUCING A POLYPEPTIDE

(75) Inventors: Andrzej Plucienniczak, Warsaw (PL); Malgorzata Kesik, Warsaw (PL); Grazyna Plucienniczak, Warsaw (PL); Diana Mikiewicz-Sygula, Czetsochowa (PL)

(73) Assignee: Instytut Biotechnologii I Antybiotykow, Warsaw (PL)

( * ) Notice: Subject to any disclaimer, the term of this patent is extended or adjusted under 35 U.S.C. 154(b) by 852 days.

(21) Appl. No.: 12/303,929

(22) PCT Filed: Jun. 8, 2007

(86) PCT No.: PCT/PL2007/000037
§ 371 (c)(1),
(2), (4) Date: Dec. 8, 2008

(87) PCT Pub. No.: WO2007/142547
PCT Pub. Date: Dec. 13, 2007

(65) Prior Publication Data
US 2010/0297773 A1    Nov. 25, 2010

(51) Int. Cl.
*C12N 15/63*    (2006.01)
*C12N 1/21*     (2006.01)
*C12N 15/74*    (2006.01)

(52) U.S. Cl.
USPC .................. 435/320.1; 435/471; 435/252.33

(58) Field of Classification Search
None
See application file for complete search history.

(56) References Cited

U.S. PATENT DOCUMENTS

| 4,952,496 A | 8/1990 | Studier et al. |
| 5,693,489 A | 12/1997 | Studier et al. |
| 2003/0061626 A1* | 3/2003 | Plaetinck et al. .......... 800/8 |

FOREIGN PATENT DOCUMENTS

WO    WO 02/46444 A2    6/2002

OTHER PUBLICATIONS

Gibson et al. Lorist2, a cosmid with transcriptional terminators insulating vector genes from interference by promoters within the insert: effect on DNA yield and cloned insert frequency. 1987. Gene. vol. 53, pp. 275-281.*
Jones et al. Tryptophan-Transducing Bacteriophages: In Vitro Studies with Restriction Endonucleases HindII+III and *Escherichia coli* Ribonucleic Acid Polymerase. Oct. 1977. Journal of Bacteriology. vol. 132, No. 1, pp. 270-281.*
Wojtowicz, Anna et al.: "Expression of Yeast Deubiquitination Enzyme UBPI Analogues in *E.Coli*", Microbian Cell Factories, Biomed Central, London, NL, vol. 4, No. 1, May 30, 2005, pp. 1-12, XP021007207.
Kwon, Young-Soon, et al.: "Viability of *E.Coli* Cells Containing Phage RNA Polymerase and Promoter: Interference of Plasmid Replication by Transcription", Genetic Analysis: Biomolecular Engineering, Elsevier Science Publishing, US, vol. 14, No. 4, Oct. 1998, pp. 133-139, XP004153554.
Plucienniczak, G., et al.: "Expression Vector pT7RS, Complete Sequence", Database NCBI [Online], Mar. 6, 2005, XP002458361. 2 pages.
Mikiewcz-Sygula, D., et al.: "Expression Vector pIGDMCT7RS, Complete Sequence", Database NCBI [Online], May 9, 2006, XP002458362. 3 pages.
Wedrychowicz, H., et al.: "Vaccine Potential of Inclusion Bodies Containing Cysteine Proteinase of *Fasciola hepatica* in Calves and Lambs Experimentally Challenged with Metacercariae of the Fluke", Veterinary Parasitology, Elsevier Science, Amsterdam, NL, vol. 147, No. 1-2, May 22, 2007 pp. 77-88, XP022089664.
Kesik, et al.: "Enteral Vaccination of Rats against *Fasciola hepatica* Using Recombinant Cysteine Proteinase (Cathepsin L1)", Vaccine, Butterworth Scientific, Guilford, GB, vol. 25, No. 18, Apr. 17, 2007, pp. 3619-3628, XP022032572.
Vethanayagam, et al.; "Decreased gene expression from T7 promoters may be due to impaired production of active T7 RNA polymerase"; Microbial Cell Factories; Jan. 7, 2005; 4(1):3.

* cited by examiner

*Primary Examiner* — Anne Gussow
*Assistant Examiner* — Channing S Mahatan
(74) *Attorney, Agent, or Firm* — Christopher L. Parmelee; Walker & Jocke

(57) ABSTRACT

The subject matters of invention relate to expression cassette, use of the expression cassette, vector, host cell, a method for producing a polypeptide ensuring its stable expression by the prokaryotic host as well as an use of the expression cassette. The invention enables stable expression of the target polypeptide, in systems where DNA-dependent RNA polymerase recognizes promoter regulating synthesis of target protein as well as selection marker, which is required for survival of the host.

11 Claims, 15 Drawing Sheets

KanPIGP

GGGGTCGACGCGGCCGCAAGGGGTGTTATGAGCCA

KanPIGk

AAAAGCTTAGAAAAACTCATCGAGCA

TermTry1

TCGACCTAAGCGGCCGCTAATCCCACAGCCGCCAGTTC

TermTry2

CGCTGGCGGCATTTT

TermTry3

GCGGAACTGGCGGCTGTGGGATTAGCGGCCGCTTAGG

TermTry4

GGCCAAAATGCCGCCA

Fig. 4a

BRESAMA

GAGGGGATCCATATGGCACGTCTAGCCTGCAAGGAAGAT

UBIBREK1

AAAAGCTTCTCGAGTTAGTAGTGTGGGAGTCCGTCAG

PA-4DP

GGGGAATTCATATGAAACGTTTTCATTATGATCGCAATAAC

PA4DKXho

AAAAGCTTCTCGAGTTATCCTATCTCATAGCCTTTTTTAG

PA-4DK

AAAAGCTTATCCTATCTCATAGCCTTTTTTAG

Fig. 4b

NdeI

*catatggcacgtctagcctgcaaggaagatcacaggtacgctatatcaacaaccaatgagatagggctac*

*atggggccgaaggtctcactaccacctggaaagaatacaaccacaatttgcaactggatgatgggaccgt*

*caaggccatctgcatggcaggttcctttaaagtcacagcacttaatgtggttagtaggaggtatctggcatca*

*ttacataaggacgctttacccacttccgtgacattcgagctcctgttcgacgggaccagcccattgaccgag*

*gaaatgggagatgacttcgggttcggactgtgtccgtatgatacgagccctgtagtcaagggaaaatacaa*

*cacaaccttgttgaatggtagtgcattctacctagtttgcccaataggtggacgggtgttatagagtgcacg*

*gcagtgagcccgacaactctgagaacagaagtggtaaagaccttcagaagagagaaaccctttccgtac*

*agaagggattgtgtgaccactacagtggaaaatgaagatctattctactgtaaatgggggggcaattggac*

*atgtgtgaaaggtgaaccagtgacctacacggggggggccagtaaaacaatgcagatggtgtggcttcgac*

*ttcaatgagcctgacggactcccacactactaactcgacctaagcggccgctaatcccacagccgcagtt*

*ccgctggcggcattttGGCCGCAAGGGGTGTTATGAGCCATATTCAACGGGAAACGTCTT

GCTCGAGGCCGCGATTAAATTCCAACATGGATGCTGATTTATATGGGTATAAATGGGC

TCGCGATAATGTCGGGCAATCAGGTGCGACAATCTATCGATTGTATGGGAAGCCCGAT

GCGCCAGAGTTGTTTCTGAAACATGGCAAAGGTAGCGTTGCCAATGATGTTACAGATG

AGATGGTCAGACTAAACTGGCTGACGGAATTTATGCCTCTTCCGACCATCAAGCATTT

TATCCGTACTCCTGATGATGCATGGTTACTCACCACTGCGATCCCCGGAAAAACAGCA

TTCCAGGTATTAGAAGAATATCCTGATTCAGGTGAAAATATTGTTGATGCGCTGGCAG

TGTTCCTGCGCCGGTTGCATTCGATTCCTGTTTGTAATTGTCCTTTTAACAGCGATCGC

GTATTTCGTCTCGCTCAGGCGCAATCACGAATGAATAACGGTTTGGTTGATGCGAGTG

ATTTTGATGACGAGCGTAATGGCTGGCCTGTTAACAAGTCTGGAAAGAAATGCATAA

ACTTTTGCCATTCTCACCGGATTCAGTCGTCACTCATGGTGATTTCTCACTTGATAACC

TTATTTTTGACGAGGGGAAATTAATAGGTTGTATTGATGTTGGACGAGTCGGAATCGC

AGACCGATACCAGGATCTTGCCATCCTATGGAACTGCCTCGGTGAGTTTTCTCCTTCAT

TACAGAAACGGCTTTTTCAAAAATATGGTATTGATAATCCTGATATGAATAAATTGCA

GTTTCATTTGATGCTCGATGAGTTTTTCT<u>AAGCTT</u>

HindIII

Fig. 7

NdeI

*catatgaaacgttttcattatgatcgcaataacatagcagttggggcggatgagtcagtagttaaggag*

*gctcatagagaagtaattaattcgtcaacagagggattattgttaaatattgataaggatataagaaaa*

*atattatcaggttatattgtagaaattgaagatactgaagggcttaaagaagttataaatgacagatatg*

*atatgttgaatatttctagtttacggcaagatggaaaaacatttatagattttaaaaaatataatgataaa*

*ttaccgttatatataagtaatcccaattataaggtaaatgtatatgctgttactaaagaaaacactattatt*

*aatcctagtgagaatggggatactagtaccaacgggatcaagaaaattttaatcttttctaaaaaaggc*

*tatgagataggataactcgacc*taagcggccgc*taatcccacagccgccagttccgctggcggcattt*

*tGGCCGCAAGGGGTGTTATGAGCCATATTCAACGGGAAACGTCTTGCTCGAGGC

CGCGATTAAATTCCAACATGGATGCTGATTTATATGGGTATAAATGGGCTCGCGAT

AATGTCGGGCAATCAGGTGCGACAATCTATCGATTGTATGGGAAGCCCGATGCGC

CAGAGTTGTTTCTGAAACATGGCAAAGGTAGCGTTGCCAATGATGTTACAGATGA

GATGGTCAGACTAAACTGGCTGACGGAATTTATGCCTCTTCCGACCATCAAGCATT

TTATCCGTACTCCTGATGATGCATGGTTACTCACCACTGCGATCCCCGGAAAAACA

GCATTCCAGGTATTAGAAGAATATCCTGATTCAGGTGAAAATATTGTTGATGCGCT

GGCAGTGTTCCTGCGCCGGTTGCATTCGATTCCTGTTTGT

Fig. 9a

Figure 1:
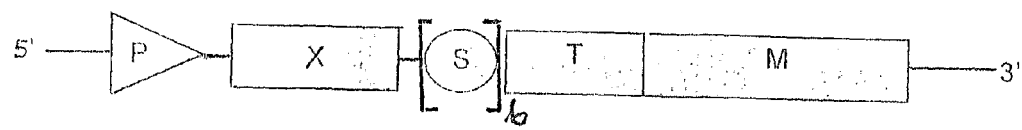

AATTGTCCTTTTAACAGCGATCGCGTATTTCGTCTCGCTCAGGCGCAATCACGAAT
GAATAACGGTTTGGTTGATGCGAGTGATTTTGATGACGAGCGTAATGGCTGGCCT
GTTGAACAAGTCTGGAAAGAAATGCATAAACTTTTGCCATTCTCACCGGATTCAGT
CGTCACTCATGGTGATTTCTCACTTGATAACCTTATTTTGACGAGGGGAAATTAA
TAGGTTGTATTGATGTTGGACGAGTCGGAATCGCAGACCGATACCAGGATCTTGC
CATCCTATGGAACTGCCTCGGTGAGTTTTCTCCTTCATTACAGAAACGGCTTTTTCA
AAAATATGGTATTGATAATCCTGATATGAATAAATTGCAGTTTCATTTGATGCTCG
ATGAGTTTTTCT<u>AAGCTT</u>
<u>HindIII</u>

Fig. 9b

<u>NdeI</u>
<u>catatg</u>aaacgttttcattatgatcgcaataacatagcagttggggcggatgagtcagtagttaaggaggct
catagagaagtaattaattcgtcaacagagggattattgttaaatattgataaggatataagaaaaatattatc
aggttatattgtagaaattgaagatactgaagggcttaaagaagttataaatgacagatatgatatgttgaat
atttctagtttacggcaagatggaaaaacatttatagattttaaaaaatataatgataaattaccgttatatataa
gtaatcccaattataaggtaaatgtatatgctgttactaaagaaaacactattattaatcctagtgagaatggg
gatactagtaccaacgggatcaagaaaattttaatcttttctaaaaaaggctatgagatagga<u>aagctt</u>

<u>HindIII</u>

Fig. 10

EXPRESSION CASSETTE, USE OF THE EXPRESSION CASSETTE, VECTOR, HOST CELL, A METHOD FOR PRODUCING A POLYPEPTIDE

The subject matters of invention relate to expression cassette, use of the expression cassette, vector, host cell, a method for producing a polypeptide ensuring its stable expression by the prokaryotic host as well as an use of the expression cassette. The invention enables stable expression of the target polypeptide, in systems where DNA-dependent RNA polymerase recognises promoter regulating synthesis of target protein as well as selection marker, which is required for survival of the host.

The possibility to produce peptides in prokaryotic systems, which were difficult and/or expensive to derive from natural sources, was the breakthrough in biotechnology. This procedure was achievable by an successful approach from the 1980's in which a system based on RNA polymerases depending on DNA was incorporated into host cells. Such cells are transformed with vectors with promoters recognised by these polymerases. One of the most widely used systems of this type is a system in which polymerase T7 recognises the promoter of T7 phage. In this system sequence encoding T7 polymerase is present in the bacterial chromosome and the recognised promoter sequence is present in the expression vector.

Such an expression system, vector and a method of expression target polypeptide were described for example in U.S. Pat. Nos. 4,952,496 and 5,693,489. In the solutions described in the cited patent descriptions, vector comprising target gene functionally linked to the promoter recognized by the RNA polymerase from T7 phage is introduced to host cell, such as *Escherichia coli*, containing gene coding phage T7 RNA polymerase. The host cells are cultivated in the known conditions enabling expression.

In many cases the system prove to be very effective and permit obtaining the high level of expression comprise even 50% of the total cell protein production [Metlitskaia L, Cabralda J E, Suleman D, Kerry C, Brinkman J, Bartfeld D, Guarna M M, Recombinant antimicrobial peptides efficiently produced using novel cloning and purification processes, Biotechnol. Appl. Biochem., (2004 June); 39(Pt 3):339-45].

However, problems are also encountered in this subject. One of them is the gradual decrease in the target gene expression which production occurs from T7 phage promoter. This problem has not been solved since the beginning of use of systems comprising T7 phage promoters.

It was previously thought that decreasing in gene expression is caused by loss or mutations of plasmid comprising a target gene. It was suggested to test the population of bacteria on their capacity to high expression of target protein [Studier F W, Moffatt B A, Use of bacteriophage T7 RNA polymerase to direct selective high-level expression of cloned genes, J. Mol. Biol. (1986) 189; 113-130; Studier F W, Rosenberg A H, Dunn J J, Dubendorff J W, Use of T7 RNA polymerase to direct expression of cloned genes, Meth. Enzymol. (1990) 185: 60-89].

Vethanayagam et al. for the first time found and described the major contributing factor to decreased expression levels in T7 based system [Vethanayagam J G and Flower A M, Decreased gene expression from T7 promoters may be due to impaired production of active T7 RNA polymerase, Microb Cell Fac. (2005 Jan. 7); 4:3]. It is connected with chromosomal mutations occurring in the area of sequence coding foreign DNA-dependent RNA polymerase of T7 phage.

Despite the above described preliminary research devoted to stable expression of the target polypeptide, in systems where DNA-dependent RNA polymerase recognises promoter regulating synthesis of the target protein a need for effective stable expression of the target polypeptide still exists. The invention solves the problems indicated above, especially the gradual decrease in the target gene expression and enabled stable expression of the target polypeptide.

According to the invention problem of stable, high level expression in systems where DNA-dependent RNA polymerase and promoter recognised by this polymerase are used, was solved by developing of system wherein polymerase recognises promoter regulating synthesis of target protein as well as selection marker, which is required for survival of the host.

The goal of the present invention is the delivery of means which could be used to obtain an expression cassette, vector, host cell and a method for the production of a polypeptide ensuring its stable expression by the prokaryotic host. A particular goal of the invention is use of the expression cassette.

The subject matter of this invention is an expression cassette containing a phage promoter functionally linked to a sequence encoding a target polypeptide as well as to a sequence encoding a selection marker, which is required for the survival of the host expressing the target polypeptide, where there is a transcriptional termination sequence for promoters other than phage promoters between the sequence encoding target polypeptide and the sequence encoding the selection marker, required for the survival of the host expressing the target polypeptide.

Preferentially, there is a translation stop codon at the 5' end upstream of the transcriptional terminator of the promoters other than phage promoters.

Preferentially, the sequence encoding a selection marker, which is required for the survival of the host expressing the target polypeptide is a sequence encoding a protein being a selection marker selected from a group comprising markers which introduce antibiotic resistance and markers which complement the genetic defect of the host cell, or their functional fragments.

Preferentially, the sequence encoding the selection marker has a modified, non-coding part at the 5' end including a Shine-Dalgarno sequence modified in such a way, that after it is transcribed to mRNA the resultant mRNA it is less recognised by ribosomes.

Preferentially, the sequence encoding the selection marker is the sequence which introduces kanamycin resistance.

Preferentially, the sequence introducing kanamycin resistance has a modified non-coding region at the 5' end, including a Shine-Dalgarno sequence modified in such a way, that after it is transcribed to mRNA, the resultant mRNA it is less recognised by ribosomes.

Preferentially, the transcription terminator for a promoter other than a phage promoter is the tryptophan terminator.

Preferentially, it contains a promoter selected from a group comprised of T7, T3, T5 and SP6 phage promoters.

Preferentially, it contains the T7 phage promoter.

Preferentially, the phage promoter is linked to a nucleotide unit whose sequence is shown in FIG. 7 and as SEQ ID NO: 7.

Preferentially, the phage promoter is linked to a nucleotide unit whose sequence is shown in FIG. 9 and as SEQ ID NO: 12.

The next subject of the invention is an use of the expression cassette comprising a phage promoter functionally linked to a sequence encoding a target polypeptide as well as to a sequence encoding a selection marker, which is required for the survival of the host expressing the target polypeptide, where there is a transcriptional termination sequence for a promoter other than a phage promoter between the sequences encoding a target polypeptide and a selection marker, which is required for the survival of the host expressing target polypeptide for vector construction in a phage polymerase/promoter system in a prokaryotic host cell.

Preferentially, there is a translational stop codon at the 5' end upstream of the transcriptional terminator sequence for promoters other than phage promoters.

The next subject of the present invention is an expression vector, characterised in that it contains an expression cassette consisting of a phage promoter functionally linked to a sequence encoding a target polypeptide as well as to a sequence encoding a selection marker, which is required for the survival of the host expressing the target polypeptide, where there is a transcriptional termination sequence for a promoter other than a phage promoter between the sequences encoding a target polypeptide and a selection marker, which is required for the survival of the host expressing target polypeptide.

Preferentially, there is a translation stop codon at the 5' end upstream of the transcriptional terminator for a promoter other than a phage promoter.

Preferentially, the sequence encoding selection marker, which is required for survival of the host expressing target polypeptide is a sequence encoding a protein as a selection marker selected from a group comprised of markers which introduce antibiotic resistance and markers which complement genetic defects of the host cell or their functional fragments.

Preferentially, the sequence encoding the selection marker has a modified non-coding region at the 5' end including a Shine-Dalgarno sequence modified in such a way, that after it is transcribed to mRNA, the resultant mRNA it is less recognised by ribosomes.

Preferentially, the sequence encoding the selection marker is a sequence which introduces kanamycin resistance.

Preferentially, the sequence introducing kanamycin resistance has a modified non-coding region at the 5' end, including a Shine-Dalgarno sequence modified in such a way, that after it is transcribed to mRNA, the resultant mRNA it is less recognised by ribosomes.

Preferentially, the transcription terminator for a promoter other than a phage promoter is the tryptophan terminator.

Preferentially, it contains a promoter selected from a group comprised of T7, T3, T5 and SP6 phage promoters.

Preferentially, it contains a T7 phage promoter.

Preferentially, it is comprised of a sequence encoding a selection marker, which is required for the survival of the host which is at the same time a selection marker enabling the selection of the cells harbouring the vector.

Preferentially, it is selected from among the following vectors: pIGCmT7KesKrE2, pIGCmT7KesPA-4D and pT7RSKesKrE2.

The next subject of the present invention is a prokaryotic host cell containing the expression vector according to any of the above claims.

Preferentially, it is a prokaryotic host cell harbouring a gene encoding an RNA polymerase which recognises the phage promoter.

Preferentially, it is an *E. coli* cell.

Preferentially, it is of the *E. coli* strain BL21(DE3).

The next subject of the invention is a method for producing a polypeptide in prokaryotic host, in a phage promoter/polymerase system characterised in that this method consists of the culturing of prokaryotic host cells containing: a) an expression vector with an expression cassette consisting of a phage promoter functionally linked to a sequence encoding target polypeptide and to a sequence encoding a selection marker, which is required for the survival of the host expressing the target polypeptide, where there is transcriptional termination sequence for a promoter other than a phage promoter between the sequence encoding the target polypeptide and the selection marker, which is required for the survival of the host expressing target polypeptide and b) a gene encoding an RNA polymerase which recognises the phage promoter, and the culturing is conducted in conditions enabling the expression of the target protein and the selection marker, and at the same time inhibiting the growth and causing the elimination of cells in which there is no expression controlled by the phage promoter.

Preferentially, the cassette has a translation stop codon at the 5' end upstream of the transcription terminator sequence for promoters other than phage promoters.

BRIEF DESCRIPTION OF THE DRAWING FIGURES

The attached figures facilitate a better understanding of the nature of the present invention.

FIG. 1 presents a scheme of an expression cassette, where P—sequence of a phage promoter, X—sequence encoding the target polypeptide, S—translation stop codon, b is equal 0 or 1, T—transcription termination sequence for promoters other than phage promoters, M—sequence encoding selection marker which is required for survival of the host expressing the target protein.

Figure 2:
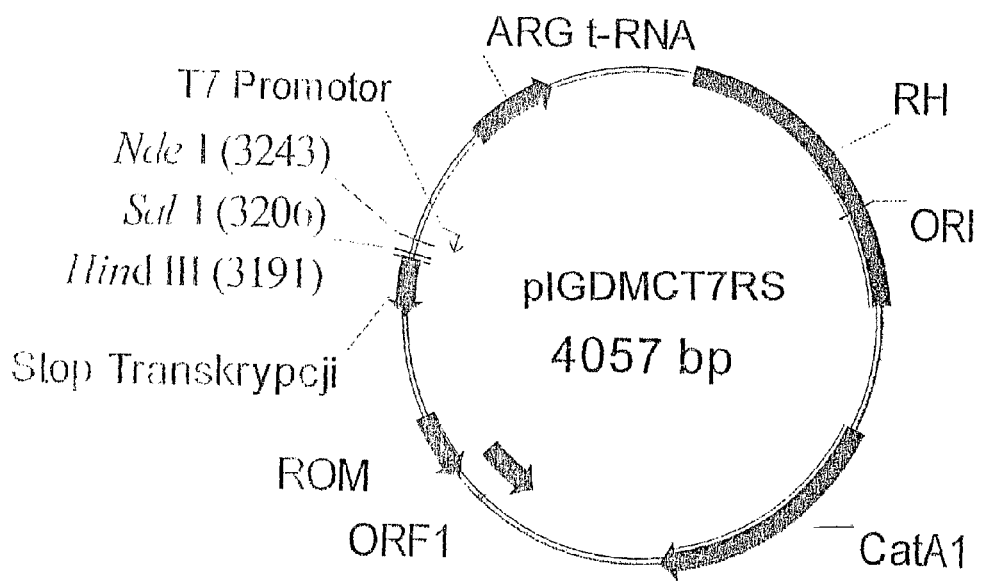

FIG. 2 presents a map of the pIGDMCT7RS plasmid, where ARG t-RNA is the gene for arginine tRNA for the AGA and AGG codons, ORI is origin of replication of the pPIGDM1 plasmid, CatA1 is the gene encoding chloramphenicol acetyl transferase, T7 is a promoter of T7 phage, stop is a termination signal for termination of transcription from T7 phage promoter.

Figure 3:
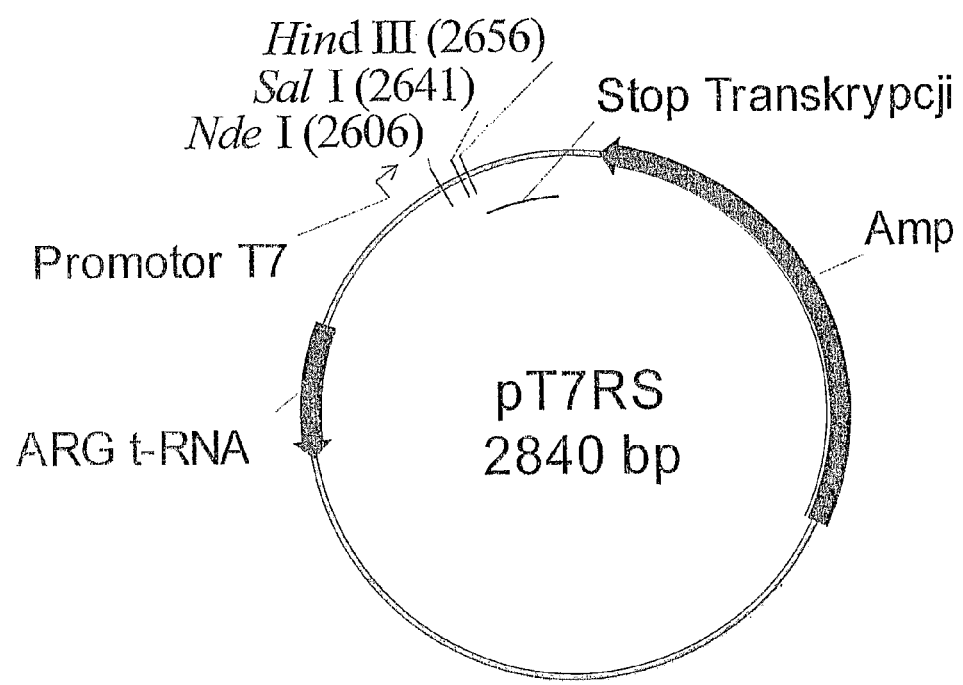

FIG. 3 presents a map of the pT7RS plasmid, where ArgU is the gene for arginine tRNA for the AGA and AGG codons, Amp is the gene encoding ampicillin resistance, T7 Promoter is a promoter of T7 phage, stop is a termination signal for termination of transcription from T7 phage promoter.

FIGS. 4a and 4b present sequences of synthetic oligonucleotides used to obtain transcription termination sequence from tryptophan operon (named: Term Try1, Term Try2, Term Try3, Term Try4) and synthetic PCR reaction primers. The sequence of the primer complementary to amplified gene is underlined.

Figure 5:
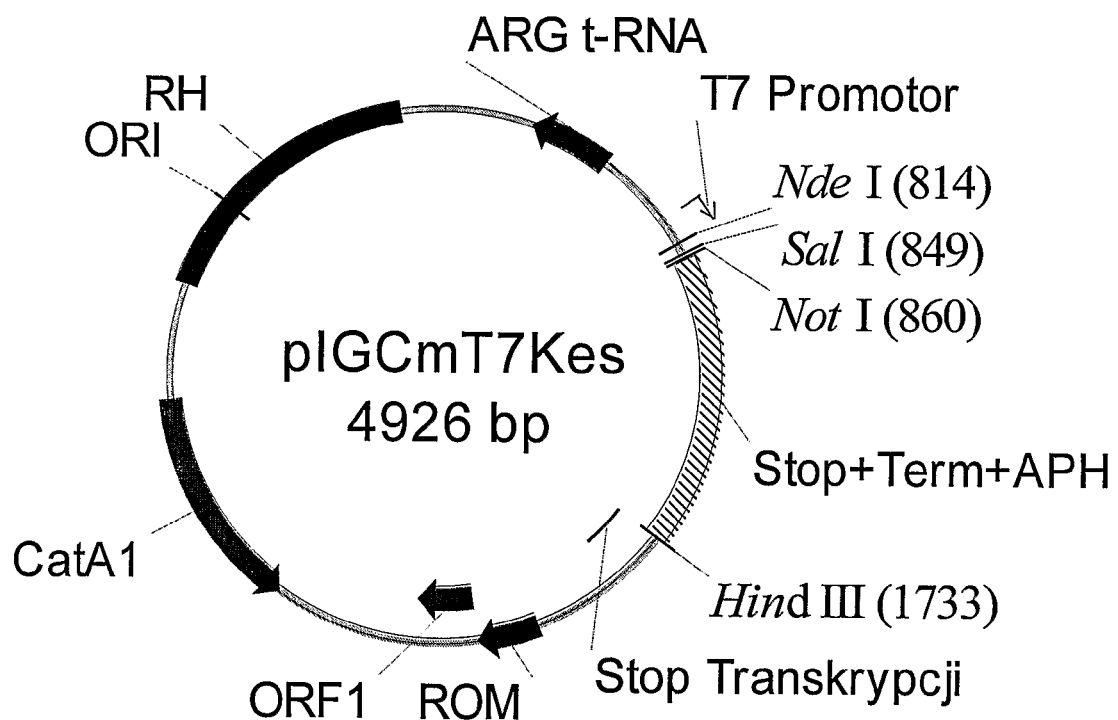

FIG. 5 presents a map of the pIGCmT7Kes plasmid, where ARG t-RNA is the gene for arginine tRNA for the AGA and AGG codons, ORI is origin of replication of the pPIGDM1 plasmid, CatA1 is the gene encoding chloramphenicol acetyl transferase, T7 promoter is a promoter of T7 phage, transcription stop is a termination signal for termination of transcription from T7 phage promoter; Stop+Term+APH– nucleotide part of the cassette, where Stop is a translational stop codon; Term is a transcriptional termination sequence from tryptophan operon (in FIG. 7 printed in boldface); APH is a modified sequence encoding aminoglycoside 3'-phosphotransferase (in FIG. 7 printed in capital letters).

Figure 6:
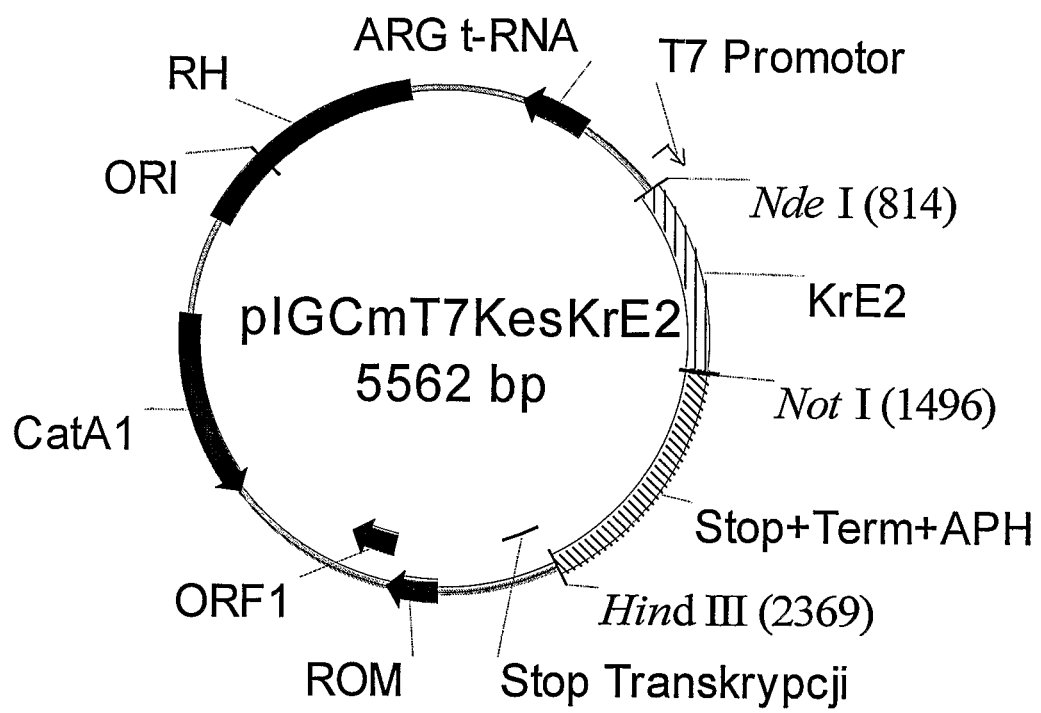

FIG. 6 presents a map of the pIGCmT7KesKrE2 plasmid with the cassette comprising T7 phage promoter and KrE2+ Stop+Term+APH nucleotide unit (shown in FIG. 7) where KrE2 is a sequence encoding a part of E2 CSFV protein; transcription stop is a termination signal for termination of transcription from T7 phage promoter; ARG t-RNA is the gene for arginine tRNA for the AGA and AGG codons, ORI is origin of replication of the pPIGDM1 plasmid, CatA1 is the gene encoding chloramphenicol acetyltransferase.

FIG. 7 presents a nucleotide unit KrE2+Stop+Term+APH cloned into pIGCmT7KesKrE2 and pT7RSKesKrE2 vectors. Sequence encoding a part of E2 CSFV (KrE2) is italicized; translational stop codon is printed in boldface; transcription termination sequence from tryptophan operon (Term) is printed in italicized boldface; gene encoding APH is printed in capital letters, non-coding modified sequence at 5' end of APH gene is printed in boldface capital letters. The unit was introduced into NdeI and HindIII restriction sites of pIGCmT7KesKrE2 vector (underlined).

Figure 8:
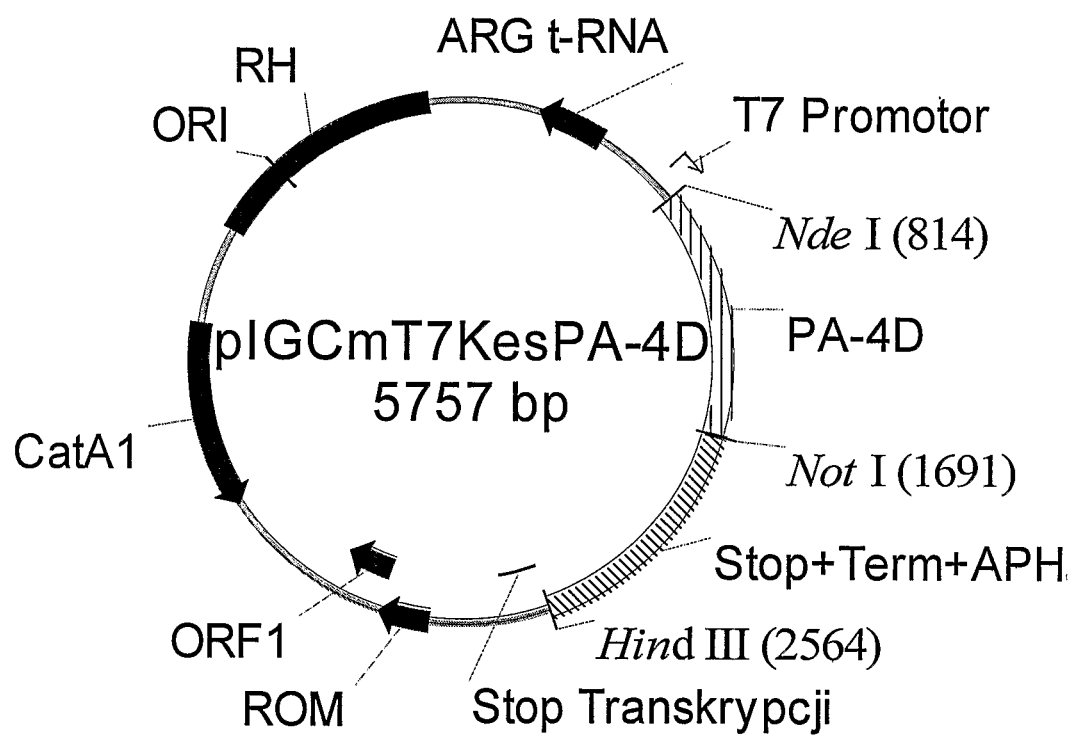

FIG. 8 presents a map of the pIGCmT7KesPA-4D plasmid with the cassette comprising T7 phage promoter and nucleotide unit PA-4D+Stop+Term+APH nucleotide unit (shown in FIG. 9) where PA-4D is a sequence encoding the *Bacillus anthracis* protective antigen domain 4; Transcription Stop is a termination signal for termination of transcription from T7 phage promoter; ARG t-RNA is the gene for arginine tRNA for the AGA and AGG codons, ORI is origin of replication of the pPIGDM1 plasmid, CatA1 is the gene encoding chloramphenicol acetyltransferase.

FIGS. 9*a* and 9*b* present a nucleotide unit PA-4D+Stop+Term+APH cloned into pIGCmT7KesPA-4D vector. Sequence encoding the *Bacillus anthracis* protective antigen 15 domain 4 (PA-4D) is italicized; translational stop codon is printed in boldface; transcription termination sequence from tryptophan operon (Term) is printed in italicized boldface; gene encoding APH is printed in capital letters, non-coding modified sequence at 5' end of APH gene is printed in boldface capital letters. The unit was introduced into NdeI and HindUI restriction sites of pIGCmT7KesPA-4D vector (underlined).

FIG. 10 presents nucleotide sequence encoding PA-4D cloned into NdeI and HindIII restriction sites of pIGCmT7PA-4D vector (underlined).

Figure 11:
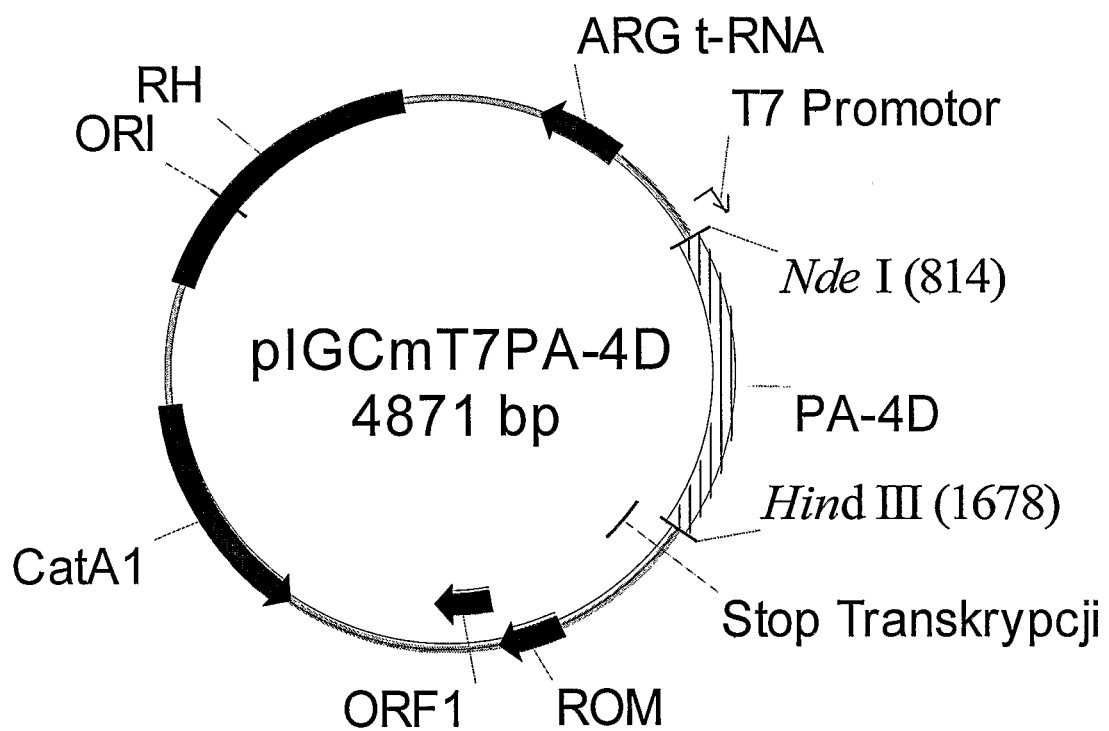

FIG. 11 presents a map of the pIGCmT7PA-4D plasmid where ARG t-RNA is the gene for arginine tRNA for AGA and AGG codons, ORI is origin of replication of the pPIGDM1 plasmid, CatA1 is the gene encoding chloramphenicol acetyltransferase, Transcription Stop is a termination signal for termination of transcription from T7 phage promoter; PA-4D is a sequence encoding the *Bacillus anthracis* protective antigen domain 4.

Figure 12:
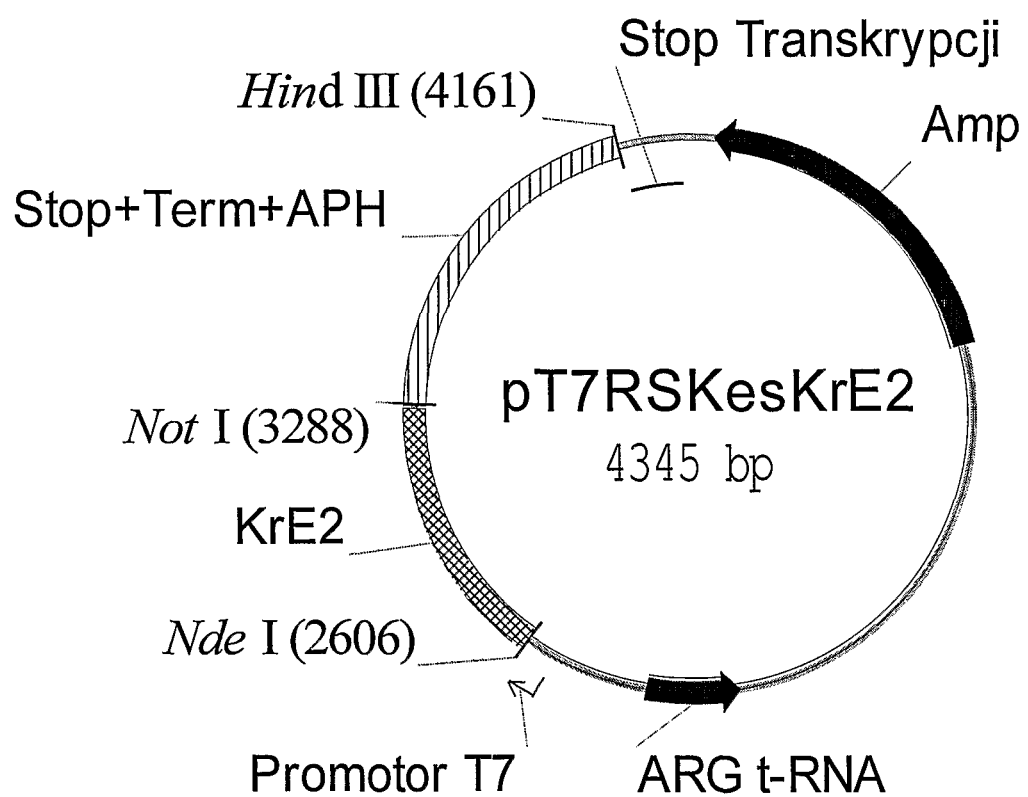

FIG. 12 presents a map of the pT7RSKesKrE2 plasmid with the cassette comprising T7 phage promoter and KrE2+Stop+Term+APH nucleotide unit (shown in FIG. 7); ARG t-RNA is the gene for arginine tRNA for the AGA and AGG codons; Amp gene encoding ampicillin resistance; transcription stop is a termination signal for termination of transcription from T7 phage promoter.

Figure 13:
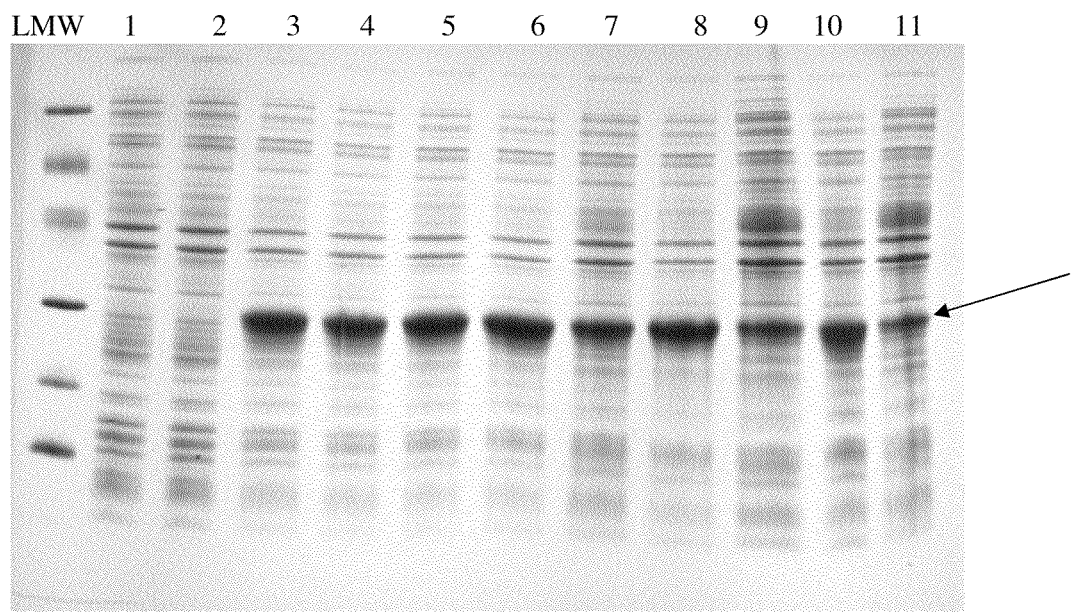
Figure 14:
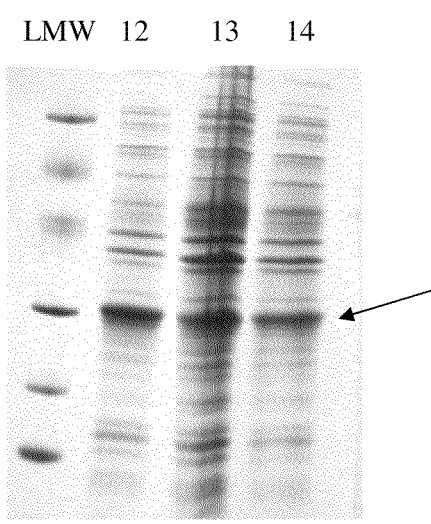

FIGS. 13 and 14 present electrophoretical separation of lysates of bacteria expressing a part of E2 CSFV (KrE2) protein.

Figure 15:
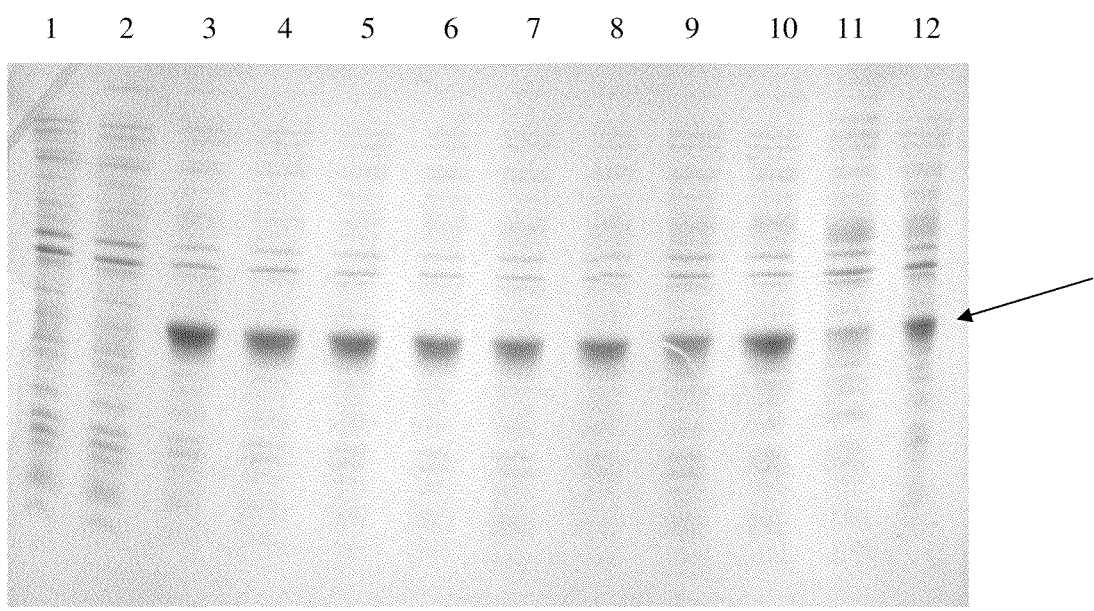

FIG. 15 presents electrophoretical separation of lysates of bacteria expressing a part of E2 CSFV (KrE2) protein.

Figure 16:
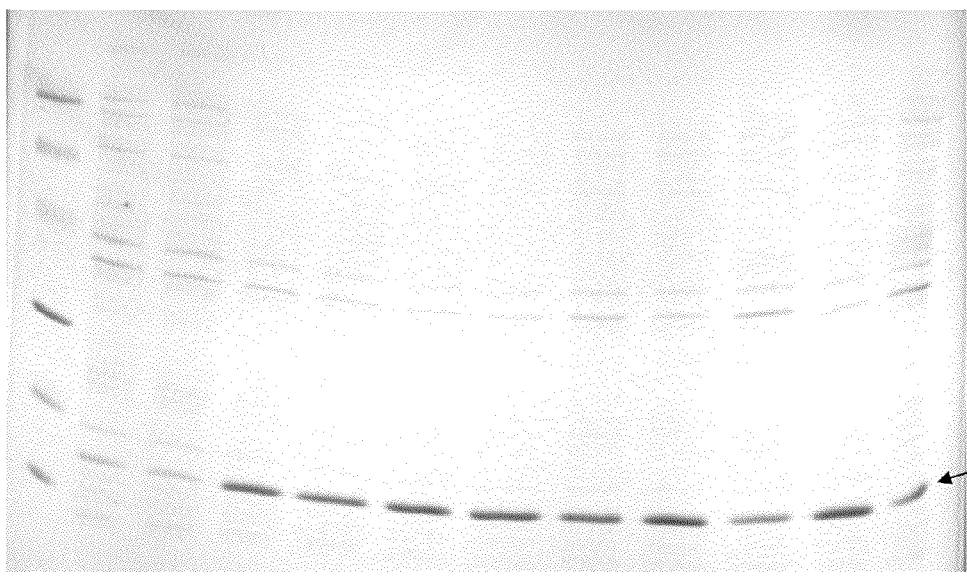
Figure 17:
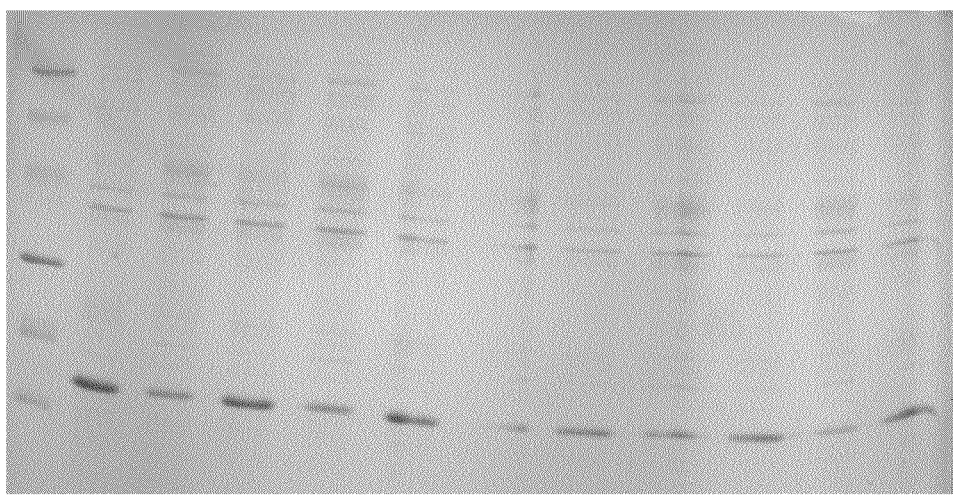

FIGS. 16 and 17 present electrophoretical separation of lysates of bacteria expressing the *Bacillus anthracis* protective antigen domain 4 (PA-4D).

DETAIL DESCRIPTION

Below are example embodiments of the above defined invention.

Example I

Construction of Cassette and pIGCmT7KesKrE2 Vector

Vectors Used for the Cassette Cloning
The cassette was cloned into two bacterial expression plasmids: pIGDMCT7RS and pT7RS.
A. pIGDMCT7RS plasmid (4057 bp) (FIG. 2, GenBank accession No. DQ485721) was created by Professor A. Plucienniczak at the Institute of Biotechnology and Antibiotics in Warsaw on the basis of the pPIGDM1 plasmid [Mikiewicz D., Wróbel B., Węgrzyn G, Plucienniczak A., Isolation and characterisation of a ColE1-like plasmid from *Enterobacter Agglomerans* with a novel variant of rom gene. Plasmid. 1997; 38(3):210-9], which belongs to a ColE1-like *Enterobacter agglomerans* group. The complete nucleotide sequence of pPIGDM1 has been determined (GenBank accession No. AF014880). The pIGDMCT7RS vector was made by introducing into pPIGDM1 the chloramphenicol acetyltransferase gene (CatA1) introducing chloramphenicol resistance, the multiple cloning site region with RNA polymerase promoter of T7 phage and the sequence encoding the transcription stop codon of T7 phage. pIGDMCT7RS plasmid carries the gene encoding AGA and AGG tRNA. The AGA and AGG tRNA supplement the shortage of these tRNA resulting from codon usage frequency in *E. coli*. The complete nucleotide sequence of pIGDMCT7RS has been determined (GenBank accession No. DQ485721). pIGDMCT7RS plasmid comprise ROM-RNA one modulator sequence; one of the genes of the ColE1 copy number control system, ORF1-rom-like ORF encoding protein exhibiting 55.7% identity to ROM protein of ColE1 plasmid and RH sequence—ColE1 homology region.
B. pT7RS plasmid (2840 bp) (FIG. 3) was created by Professor A. Plucienniczak at the Institute of Biotechnology and Antibiotics in Warsaw. The complete nucleotide sequence of pT7RS has been determined (GenBank accession No. AY923866). The pT7RS vector contains RNA polymerase promoter of T7 phage and the sequence encoding the transcriptional stop codon of T7 phage. The pT7RS carries the gene encoding AGA and AGG tRNA.
A Method of Obtaining pIGCmT7KesKrE2
Stage I.
A plasmid was used as a template of the aminoglycoside 3' phosphotransferase (APH) gene, responsible for resistance to antibiotics kanamycin. The sequence was amplified with the sense KanPIGP primer (sequence shown in the FIG. 4 and as SEQ ID NO: 1) and antisense KanPIGk primer (sequence shown in the FIG. 4 and as SEQ ID NO: 2). The KanPIGP primer was designed to introduce SalI and NotI restriction sites. The KanPIGk primer introduce HindIII site and TAA stop codon. Additionally, the KanPIGP primer modify Shine-Dalgarno sequence in such a way, that after it is transcribed to mRNA, the resultant mRNA it is worse recognised by ribosomes. The modifications are as follow: in the non-coding part of the gene which encode aminoglycolyside-3' phosphotransferase (APH) five nucleotides were altered: adenine to guanine at position 12; thymine to cytosine at position 13; adenine to cytosine at position 14; adenine to guanine at position 15; thymine to guanine at position 16.

The resulting PCR product was separated by PAGE, isolated, digested with SalI and HindIII and deproteinised. Obtained fragment was ligated into SalI and HindIII-digested pIGDMCT7RS vector. The validity of the sequence of the gene introduced into pIGDMCT7RS vector was confirmed by sequencing.

Stage II.

Following synthetic oligonucleotides TermTry1, TermTry2, TermTry3 and TermTry4 (sequences shown in FIG. 4 and as seq. No. 3, 4, 5, and 6 respectively) were ligated in order to form synthetic tryptophan terminator. The TermTry1 oligonucleotide introduces SalI and NotI sites and TAA translation stop codon and the TermTry4 introduces NotI site. The resulting 57 bp-long product was separated by PAGE, isolated and digested with SalI, NotI. The obtained fragment was ligated into the final vector obtained in stage I digested with the same enzymes. The validity of the sequence introduced into the vector was confirmed by sequencing. As the result described in the stage I and II of the experiment vector pIGCmT7Kes was obtained. A scheme of this vector with marked nucleotide fragment Stop+Term+APH, consisting a part of sequence shown in FIG. 7, was shown in FIG. 5.

Stage III.

A plasmid comprising whole nucleotide sequence of E2 antigen of CSFV virus was used in PCR amplification with the sense BRESAMA primer (sequence shown in FIG. 4 and as SEQ ID NO: 8) and reverse UBIBREK1 primer (sequence shown in FIG. 4 and as SEQ ID NO: 9) of 1023 bp fragment corresponding to nt 2428-3087, according to coordinates of GeneBank sequences of E2 gene (accession No. M31768). The BRESAMA and UBIBREK1 primers were designed on the basis of coding sequence of E2 gene of CSFV virus. The sequence coding the transmembrane part of E2 protein was not amplified. The sense BRESAMA primer introduces the changes in the nucleotide sequence at the 5' end of DNA molecule, altering guanine to thymine at position 2430. The introduced modification in nucleotide sequence does not change the amino acid sequence. Additionally, BRESAMA primer elongates 5' end of DNA molecule introducing alanine codon (GCA) and recognition sites for NdeI and BamHI restriction nucleases. The UBIBREK1 primer elongate 3' end of DNA molecule introducing TAA translation stop codon and recognition sites for HindIII and XhoI restriction nucleases. Following the PCR, the mixture was separated by PAGE and isolated. The amplified fragment, 1058 bp long was eluted from polyacrylamide gel and than digested with the restriction nucleases NdeI and HindIII and deproteinized. The resultant fragment (KrE2) was ligated with NdeI and HindIII-digested and deproteinized pIGCmT7Kes vector. The validity of the sequence introduced into the vector was confirmed by sequencing. As a result of the procedure the pIGCmT7KesKrE2 vector (FIG. 6) with expression cassette comprising KrE2+Stop+Term+APH nucleotide unit (shown in FIG. 7 and as SEQ ID NO: 7) under transcriptional control of the T7 promoter was obtained.

Example II

Construction of Vectors pIGCmT7KesPA-4D and pIGCmT7PA-4D (Comparative Vector)

The plasmid comprising the whole nucleotide sequence of Bacillus anthracis protective antigen domain 4 (GeneBank accession No. M31768) was used in PCR reaction to amplified, with the use of sense PA-4DP primer (sequence shown in FIG. 4 and as SEQ ID NO: 10) and reverse PA4DKXho primer (sequence shown in FIG. 4 and as SEQ ID NO: 11), 429 bp DNA fragment according to coordinates of GeneBank sequences of the gene (accession No. AF065404). The PA-4DP and PA4DKXho primers were designed on the basis of coding sequence of Bacillus anthracis protective antigen domain 4. The sense primer introduces recognition sites for EcoRI and NdeI restriction nucleases, the antisense primer introduce recognition site for XhoI restriction nuclease. Following the PCR the mixture was separated electrophoretically on a polyacrylamide gel. The amplified DNA fragment was eluted from the polyacrylamide gel, and digested with the restriction nuclease NdeI and XhoI and deproteinised. The obtained fragment was ligated with the vector pIGCmT7Kes, digested with the same restriction nucleases and deproteinised. The validity of the sequence introduced into the vector was confirmed by sequencing. As a result of the procedure the pIGCmT7KesPA-4D vector (FIG. 8) with the expression cassette comprising nucleotide PA-4D+Stop+Term+APH unit (shown in FIG. 9 and as SEQ ID NO: 12) under transcriptional control of the T7 promoter was obtained. The validity of the sequence introduced into the vector was confirmed by sequencing.

The plasmid comprising the whole nucleotide sequence of Bacillus anthracis protective antigen domain four was used in PCR reaction to amplified, with the use of sense PA-4DP primer (sequence shown in FIG. 4 and as SEQ ID NO: 10) and antisense PA4DK primer (sequence shown in FIG. 4 and as SEQ ID NO: 13), 429 bp DNA fragment according to coordinates of GeneBank sequences of the gene (accession No. AF065404). The PA-4D and PA4DK primers were designed on the basis of coding sequence of Bacillus anthracis protective antigen domain four. The sense primer introduces recognition sites for EcoRI and NdeI restriction nucleases, the antisense primer introduce recognition site for HindIII restriction nuclease. Following the PCR the mixture was separated electrophoretically on a polyacrylamide gel. The amplified DNA fragment was eluted from the polyacrylamide gel, and digested with the restriction nuclease NdeI and HindIII and deproteinised. The obtained fragment (sequence shown in FIG. 10 and as SEQ ID NO: 14) was ligated with the pIGDMCT7RS vector, digested with the same restriction nucleases and deproteinised. The validity of the sequence introduced into the vector was confirmed by sequencing. As a result of the procedure the pIGCmT7PA-4D vector was obtained (FIG. 11).

Example III

Construction of pT7RSKesKrE2 Vector

A segment consisting of the sequences encoding a part of E2 CSFV protein (KrE2), the tryptophane terminator and APH was digested out of the pIGCmT7KesKrE2 with NdeI and HindIII restriction nucleases. This fragment was ligated to pT7RS vector digested with the same restriction nucleases and deproteinised following digestion. The validity of the sequence introduced into the vector was confirmed by sequencing. As a result of the procedure the pT7RSKesKrE2 vector (FIG. 12) with the expression cassette comprising KrE2+Stop+Term+APH nucleotide unit (shown in FIG. 7 and as SEQ ID NO: 7) under transcriptional control of the T7 promoter was obtained.

Example IV

Expression System and its Operation

Operation of the system in the presence of expression cassette in vectors according to the invention, in which expression is based on T7 phage promoter, has been tested for two different target polypeptides and two expression vectors.

The used sequences encoding recombinant proteins originate from two organisms: E2(KrE2) protein from virus and PA-4D protein from bacteria.

Plasmids comprising the verified insert were transformed into E. coli cells strain BL21(DE3).

In the chromosome of E. coli BL21(DE3) strain and its derivatives there is a gene encoding RNA polymerase of T7 phage under the control of lacUV5 promoter. The gene is recognised by the bacterial RNA polymerase. There is an operator sequence between the promoter and the gene encoding T7 RNA polymerase which binds repressor protein in that manner blocking the initiation of transcription. Only when repressor binds to IPTG, which leads to loss of protein affinity to operator site, that the transcription of phage polymerase gene may start. Phage polymerase transcribe a gene in an expression vector under the control of promoter recognised by T7 bacteriophage RNA polymerase.

E. coli cells were transformed using transformation method of competent cells described by Chung i Miller [Chung C T, Miller R H. A rapid and convenient method for preparation and storage of competent bacterial cells. Nucleic Acids Res. 1988 Apr. 25; 16(8):3580].

Design of Experiments

Three experiments were conducted in which:

1. E. coli bacteria carrying pIGCmT7KesKrE2 plasmid were cultivated.
2. E. coli bacteria carrying pT7RSKesKrE2 plasmid were cultivated.
3. E. coli bacteria carrying pIGCmT7KesPA-4D plasmid and E. coli bacteria carrying pIGCmT7PA-4D plasmid were cultivated.

In the experiment 1 an expression level of KrE2 protein in E. coli harbouring pIGCmT7KesKrE2 plasmid in a culture containing chloramphenicol as a selection marker (select out bacteria harbouring expression vector) in relation to an expression level of KrE2 protein in a culture containing kanamycin as a selection marker (select out bacteria harbouring expression vector and expressing the KrE2 protein) was examined.

In the experiment 2 an expression level of KrE2 protein in E. coli harbouring pT7RSKesKrE2 plasmid in a culture containing ampicillin as a selection marker (select out bacteria harbouring expression vector) in relation to an expression level of KrE2 protein in a culture containing kanamycin as a selection marker (select out bacteria harbouring expression vector and expressing the KrE2 protein) was examined.

In the experiment 3 an expression level of PA-4D protein in E. coli harbouring pIGCmT7PA-4D plasmid in a culture containing chloramphenicol as a selection marker (select out bacteria harbouring expression vector) in relation to E. coli harbouring pIGCmT7KesPA-4D plasmid in a culture containing kanamycin as a selection marker (select out bacteria harbouring expression vector and expressing the PA-4D protein) was examined. Additionally, in this experiment the expression level of target polypeptide obtained in a commonly used system comprising T7 phage promoter and the expression level of target polypeptide obtained in the system according to the invention. To this end standard vector with T7 phage promoter in which sequence encoding PA-4D was introduced (pIGCmT7PA-4D) and modified vector (pIGCmT7KesPA-4D) containing sequence encoding PA-4D as a part of nucleotide cassette segment was used according to the invention.

In each experiment the protein expression was conducted. To this end E. coli bacteria strain BL21(DE3) harbouring the recombinant plasmid were grown in 3 ml of LB broth containing chloramphenicol (17 μg/ml) at 37° C. for 3 hours, diluted with fresh broth (1:100) containing kanamycin (25 μg/ml) and shaked at 37° C. till $A_{600}$ reached 0.4. Next the target polypeptide was induced by addition of isopropylthiogalactoside (IPTG 0.1 mM final concentration) and shaking was continued for 18 more hours. Samples for $A_{600}$ measurements and for a electrophoretical separation on polyacrylamide gel (SDS-PAGE) were taken every 2 hours in the time course of culturing conducted following the induction. The presence and amount of target polypeptide was analysed by bacterial lysate separation on 15% polyacrylamide gel (SDS-PAGE) carried out as described by Laemmli [Laemmli U K. Cleavage of structurals proteins during the assembly of the head of bacteriophage T4. Nature. 1970 Aug. 15; 227(5259): 680-5].

The separated proteins were visualised by staining with Coomassie Brilliant Blue G Electrophoretical separation of lysates of bacterial cell samples taken during the experiment 1 are shown in FIGS. 13 and 14.

Lines:

LMW—Molecular weight protein markers for electrophoresis. It contains 97, 66, 45, 30, 20.1 and 14.4 kDa polypeptides.

1—Cell lysate of E. coli bacteria transformed with pIGCmT7KesKrE2 vector. Bacteria were cultured in medium without kanamycin (Km⁻) and with chloramphenicol (Cm⁺). Uninduced.

2—Cell lysate of E. coli bacteria transformed with pIGCmT7KesKrE2 vector. Bacteria were cultured in medium with kanamycin (Km⁺). Uninduced.

3, 5, 7, 9, 11, 13—Cell lysate of E. coli bacteria transformed with pIGCmT7KesKrE2 vector. Bacteria were cultured in medium Km⁻, Cm⁺. Samples of culture taken every 2 hours following the induction.

4, 6, 8, 10, 12, 14—Cell lysate of E. coli bacteria transformed with pIGCmT7KesKrE2 vector. Bacteria were cultured in medium Km⁺. Samples of culture were taken every 2 hours following the induction.

The expression level of KrE2 is marked by arrow on the electrophoretical separations. It is seen that expression level of this protein in the time course of culturing conducted without kanamycin diminishes comparing with expression level of this protein in culture containing kanamycin. The difference in the expression level is seen in lines of electrophoretically separated lysates of bacteria taken already 6 hours after induction of target protein expression.

This difference in expression levels grows as time passes.

Electrophoretical separation of lysates of bacterial cell samples taken during the experiment 2 are shown in FIG. 15.

Lines:

1—Cell lysate of E. coli bacteria transformed with pT7RSKesKrE2 vector. Bacteria were cultured in medium without kanamycin (Km⁻) and with ampicillin (Amp⁺). Uninduced.

2—Cell lysate of E. coli bacteria transformed with pT7RSKesKrE2 vector. Bacteria were cultured in medium with kanamycin (Km⁺). Uninduced.

3, 5, 7, 9, 11. —Cell lysate of E. coli bacteria transformed with pT7RSKesKrE2 vector. Bacteria were cultured in medium Km⁻, Amp⁺. Samples of culture taken every 2 hours following the induction.

4, 6, 8, 10, 12. —Cell lysate of E. coli bacteria transformed with pT7RSKesKrE2 vector. Bacteria were cultured in medium Km⁺. Samples of culture were taken every 2 hours following the induction.

The expression level of KrE2 is marked by arrow on the electrophoretical separations. It is seen that expression level of this protein in the time course of culturing conducted without kanamycin diminishes comparing with expression level of this protein in culture containing kanamycin. The difference in the expression level is seen in lines of electrophoretically separated lysates of bacteria taken already 8 hours after induction of target protein expression.

This difference in expression levels grows as time passes.

Electrophoretical separation of lysates of bacterial cell samples taken during the experiment 3 are shown in FIGS. 16 and 17.

Lines:

LMW—Molecular weight protein markers for electrophoresis. It contains 97, 66, 45, 30, 20.1 and 14.4 kDa polypeptides.

1. Cell lysate of *E. coli* bacteria transformed with pIGCmT7KesPA-4D vector. Bacteria were cultured in medium with kanamycin (Km$^+$). Uninduced.

2. Cell lysate of *E. coli* bacteria transformed with pIGCmT7PA-4D vector. Bacteria were cultured in medium with chloramphenicol. Uninduced.

3, 5, 7, 9, 11, 13, 15, 17, 19, 21. Cell lysate of *E. coli* bacteria transformed with pIGCmT7PA-4D vector. Bacteria were cultured in medium with chloramphenicol. Samples of culture were taken every 2 hours following the induction.

4, 6, 8, 10, 12, 14, 16, 18, 20, 22. Cell lysate of *E. coli* bacteria transformed with pIGCmT7KesPA-4D vector. Bacteria were cultured in medium with kanamycin. Samples of culture were taken every 2 hours following the induction.

The expression level of PA-4D is marked by arrow on the electrophoretical separations. It is seen that expression level of this protein in the time course of culturing conducted without kanamycin (culture with chloramphenicol) diminishes comparing with expression level of this protein in culture containing kanamycin. The difference in the expression level is already seen in lines of electrophoretically separated lysates of bacteria taken 8 hours after induction of target protein expression. This difference in expression levels grows as time passes.

Additionally, in this experiment the expression level of target polypeptide obtained in commonly used system containing solely promoter of T7 phage was compared with the expression level of the target polypeptide obtained in the system according the invention. To this end two vectors were used: the standard vector with T7 phage promoter and with cloned sequence encoding PA-4D (pIGCmT7PA-4D) and the modified vector (pIGCmT7KesPA-4D) comprising PA-4D coding sequence as a part of nucleotide unit of the cassette according to the invention. Analysis of electrophoretical separations of samples taken at early stages of cultivation (first 4 hours after induction of expression of the target polypeptide) shows that expression of the target protein is on the same level in the standard system employing T7 phage promoter and in the system described in the invention. It is possible because in the system according to the invention high level of expression, typical for T7 phage promoter, is directed mainly at the target promoter.

In the process conducted as described in the invention bacteria cells in whose chromosome occurred a mutation causing lack of production of functional T7 phage polymerase and/or bacteria in which, due to a mutation, T7 phage promoter lost its functionality, are eliminated from the culture. Functional polymerase and a T7 phage promoter recognised by that polymerase are prerequisites for obtaining expression of the target polypeptide. This means, that from the culture are eliminated bacteria cells not producing the target polypeptide, which otherwise would grow and divide faster. Therefore the invention allows to prevent the culture from being dominated by the bacteria not expressing the target polypeptide.

The invention claimed is:

1. An expression cassette containing a phage promoter and a sequence encoding a target polypeptide, wherein the cassette is presented with the formula P-X-(S)$_b$T-M, wherein P means the sequence of the phage promoter, X means a target sequence, S means translation stop codon, b=1 (present) or b=0 (absent) in the cassette sequence, T means transcriptional termination sequence for promoters other than phage promoters and M means a sequence encoding a selection marker, required for the survival of a host expressing the target polypeptide, and wherein the sequence M, encoding the selection marker, located in the cassette, is a sequence encoding a protein being a selection marker selected from a group comprising markers which introduce antibiotic resistance, and wherein the sequence encoding the selection marker is a sequence that introduces kanamycin resistance, wherein the cassette includes only a single promoter, which single promoter consists of the phage promoter, wherein the schema of the cassette is:

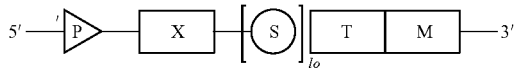

wherein the sequence encoding the selection marker encodes aminoglycolyside-3' phosphotransferase (APH), wherein the sequence encoding the selection marker has a modified, non-coding part at the 5' end including a Shine-Dalgarno sequence, wherein said Shine-Dalgarno sequence has five altered nucleotides, wherein starting from the 5' end the altered nucleotides are: thymine to guanine; adenine to guanine; adenine to cytosine; thymine to cytosine; and adenine to guanine.

2. The cassette according to claim 1, wherein the cassette contains a promoter selected from a group comprised of T7, T3, T5 and SP6 phage promoters, preferably the T7 phage promoter.

3. The expression cassette containing a phage promoter and a sequence encoding a target polypeptide, wherein the cassette is presented with the formula P-X-(S)$_b$T-M, wherein P means the sequence of the phage promoter, X means a target sequence, S means translation stop codon, b=1 (present) or b=0 (absent) in the cassette sequence, T means transcriptional termination sequence for promoters other than phage promoters and M means a sequence encoding a selection marker, required for the survival of a host expressing the target polypeptide, and wherein a translation stop codon S is at the 5' end upstream of the transcriptional termination sequence T of the promoters, and wherein the sequence M, encoding the selection marker, located in the cassette, is a sequence encoding a protein being a selection marker selected from a group comprising markers which introduce antibiotic resistance, and wherein the sequence encoding the selection marker is a sequence that introduces kanamycin resistance, wherein the schema of the cassette is:

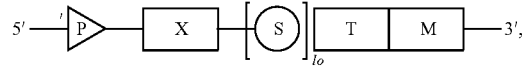

wherein the phage promoter is linked to a nucleotide unit whose sequence is SEQ ID NO: 7.

4. The expression cassette containing a phage promoter and a sequence encoding a target polypeptide, wherein the cassette is presented with the formula P-X-(S)$_b$T-M, wherein P means the sequence of the phage promoter, X means a target sequence, S means translation stop codon, b=1 (present) or b=0 (absent) in the cassette sequence, T means transcriptional termination sequence for promoters other than phage promoters and M means a sequence encoding a selection marker, required for the survival of a host expressing the target polypeptide, and wherein a translation stop codon S is at the 5' end upstream of the transcriptional termination sequence T of the promoters, and wherein the sequence M, encoding the selection marker, located in the cassette, is a sequence encoding a protein being a selection marker selected from a group comprising markers which introduce antibiotic resistance, and wherein the sequence encoding the selection marker is a sequence that introduces kanamycin resistance, wherein the schema of the cassette is:

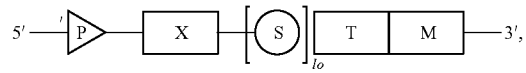

wherein the phage promoter is linked to a nucleotide unit whose sequence is SEQ ID NO: 12.

5. An expression vector comprising an expression cassette presented with the formula P-X-(S)$_b$T-M, wherein P means the sequence of the phage promoter, X means a target sequence, S means translation stop codon, b=1 (present) or b=0 (absent) in the cassette sequence, T means transcriptional termination sequence for promoters other than phage promoters and M means a sequence encoding a selection marker, required for the survival of a host expressing the target polypeptide, wherein the sequence encoding selection marker M, located in the cassette, is a sequence encoding a protein as a selection marker selected from a group comprised of markers which introduce antibiotic resistance, wherein the sequence encoding the selection marker M is a sequence that introduces kanamycin resistance, and wherein the sequence encoding selection marker M, located in the cassette, which is at the same time a selection marker enabling the selection of the cells harbouring the vector, wherein the cassette includes only a single promoter, which single promoter consists of the phage promoter, wherein the sequence encoding the selection marker encodes aminoglycolyside-3' phosphotransferase (APH), wherein the sequence encoding the selection marker has a modified non-coding region at the 5' end including a Shine-Dalgarno sequence, wherein said Shine-Dalgarno sequence has five altered nucleotides, wherein starting from the 5' end the altered nucleotides are: thymine to guanine; adenine to guanine; adenine to cytosine; thymine to cytosine; and adenine to guanine.

6. The vector according to claim 5, wherein the vector contains a promoter selected from a group comprised of T7, T3, T5 and SP6 phage promoters, preferably the T7 phage promoter.

7. An expression vector comprising an expression cassette presented with the formula $P-X-(S)_b T-M$, wherein P means the sequence of the phage promoter, X means a target sequence, S means translation stop codon, b=1 (present) or b=0 (absent) in the cassette sequence, T means transcriptional termination sequence for promoters other than phage promoters and M means a sequence encoding a selection marker, required for the survival of a host expressing the target polypeptide, wherein the sequence encoding selection marker M, located in the cassette, is a sequence encoding a protein as a selection marker selected from a group comprised of markers which introduce antibiotic resistance, wherein the sequence encoding the selection marker M is a sequence that introduces kanamycin resistance, and wherein the sequence encoding selection marker M, located in the cassette, which is at the same time a selection marker enabling the selection of the cells harbouring the vector, wherein the cassette includes only a single promoter, which single promoter consists of the phage promoter, wherein the vector is selected from among the following vectors: pIGCmT7KesKrE2, pIGCmT7KesPA-4D and pT7RSKesKrE2.

8. A prokaryotic host cell containing the expression vector according to any of claim 5, 6, or 7.

9. The cell according to claim 8, wherein the cell is a prokaryotic host cell harbouring a gene encoding an RNA polymerase which recognises the phage promoter.

10. The cell according to claim 8, wherein the cell is an *E. coli* cell.

11. The cell according to claim 10, wherein the cell is an *E. coli* strain BL21(DE3).

\* \* \* \* \*

SEQUENCE LISTING

```
<160> NUMBER OF SEQ ID NOS: 14

<210> SEQ ID NO 1
<211> LENGTH: 35
<212> TYPE: DNA
<213> ORGANISM: Artificial
<220> FEATURE:
<223> OTHER INFORMATION: primer KanPIGP

<400> SEQUENCE: 1
ggggtcgacg cggccgcaag gggtgttatg agcca                              35

<210> SEQ ID NO 2
<211> LENGTH: 26
<212> TYPE: DNA
<213> ORGANISM: Artificial
<220> FEATURE:
<223> OTHER INFORMATION: primer KanPIGk

<400> SEQUENCE: 2
aaaagcttag aaaaactcat cgagca                                        26

<210> SEQ ID NO 3
<211> LENGTH: 38
<212> TYPE: DNA
<213> ORGANISM: Artificial
<220> FEATURE:
<223> OTHER INFORMATION: oligonucleotide Term Try1
```

<400> SEQUENCE: 3
tcgacctaag cggccgctaa tcccacagcc gccagttc                          38

<210> SEQ ID NO 4
<211> LENGTH: 15
<212> TYPE: DNA
<213> ORGANISM: Artificial
<220> FEATURE:
<223> OTHER INFORMATION: oligonucleotide Term Try2

<400> SEQUENCE: 4
cgctggcggc attttt                                                 15

<210> SEQ ID NO 5
<211> LENGTH: 37
<212> TYPE: DNA
<213> ORGANISM: Artificial
<220> FEATURE:
<223> OTHER INFORMATION: oligonucleotide Term Try3

<400> SEQUENCE: 5
gcggaactgg cggctgtggg attagcggcc gcttagg                          37

<210> SEQ ID NO 6
<211> LENGTH: 16
<212> TYPE: DNA
<213> ORGANISM: Artificial
<220> FEATURE:
<223> OTHER INFORMATION: oligonucleotide Term Try 4

<400> SEQUENCE: 6
ggccaaaatg ccgcca                                                 16

<210> SEQ ID NO 7
<211> LENGTH: 1562
<212> TYPE: DNA
<213> ORGANISM: Artificial
<220> FEATURE:
<223> OTHER INFORMATION: nucleotide fragment KrE2+Stop+Term+APH

<400> SEQUENCE: 7
catatggcac gtctagcctg caaggaagat cacaggtacg ctatatcaac aaccaatgag    60
atagggctac atggggccga aggtctcact accacctgga agaatacaa ccacaatttg   120 caactggatg atgggaccgt caaggccatc tgcatggcag gttcctttaa agtcacagca   180
cttaatgtgg ttagtaggag gtatctggca tcattacata aggacgcttt acccacttcc   240
gtgacattcg agctcctgtt cgacgggacc agcccattga ccgaggaaat gggagatgac   300
ttcgggttcg gactgtgtcc gtatgatacg agccctgtag tcaagggaaa atacaacaca   360
accttgttga atggtagtgc attctaccta gtttgcccaa tagggtggac gggtgttata   420
gagtgcacgg cagtgagccc gacaactctg agaacagaag tggtaaagac cttcagaaga   480
gagaaaccct ttccgtacag aagggattgt gtgaccacta cagtgaaaa tgaagatcta   540 ttctactgta aatggggggg caattggaca tgtgtgaaag gtgaaccagt gacctacacg   600
ggggggccag taaaacaatg cagatggtgt ggcttcgact tcaatgagcc tgacggactc   660
ccacactact aactcgacct aagcggccgc taatcccaca gccgcagtt ccgctggcgg   720 catttttggcc gcaaggggtg ttatgagcca tattcaacgg gaaacgtctt gctcgaggcc   780
gcgattaaat tccaacatgg atgctgattt atatgggtat aaatgggctc gcgataatgt   840
cgggcaatca ggtgcgacaa tctatcgatt gtatgggaag cccgatgcgc cagagttgtt   900

-continued

```
tctgaaacat ggcaaaggta gcgttgccaa tgatgttaca gatgagatgg tcagactaaa       960
ctggctgacg gaatttatgc ctcttccgac catcaagcat tttatccgta ctcctgatga      1020
tgcatggtta ctcaccactg cgatccccgg aaaaacagca ttccaggtat tagaagaata     1080
tcctgattca ggtgaaaata ttgttgatgc gctggcagtg ttcctgcgcc ggttgcattc     1140
gattcctgtt tgtaattgtc cttttaacag cgatcgcgta tttcgtctcg ctcaggcgca     1200
atcacgaatg aataacggtt tggttgatgc gagtgatttt tgatgacgagc gtaatggctg     1260 gcctgttgaa caagtctgga agaaatgca taaacttttg ccattctcac cggattcagt     1320
cgtcactcat ggtgatttct cacttgataa ccttattttt gacgagggga aattaatagg     1380
ttgtattgat gttggacgag tcggaatcgc agaccgatac caggatcttg ccatcctatg     1440
gaactgcctc ggtgagtttt ctccttcatt acagaaacgg cttttcaaa aatatggtat     1500 tgataatcct gatatgaata aattgcagtt tcatttgatg ctcgatgagt ttttctaagc     1560
tt                                                                    1562
```

```
<210> SEQ ID NO 8
<211> LENGTH: 39
<212> TYPE: DNA
<213> ORGANISM: Artificial
<220> FEATURE:
<223> OTHER INFORMATION: primer BRESAMA

<400> SEQUENCE: 8
gaggggatcc atatggcacg tctagcctgc aaggaagat                             39

<210> SEQ ID NO 9
<211> LENGTH: 37
<212> TYPE: DNA
<213> ORGANISM: Artificial
<220> FEATURE:
<223> OTHER INFORMATION: primer UBIBREK1

<400> SEQUENCE: 9
aaaagcttct cgagttagta gtgtgggagt ccgtcag                               37

<210> SEQ ID NO 10
<211> LENGTH: 41
<212> TYPE: DNA
<213> ORGANISM: Artificial
<220> FEATURE:
<223> OTHER INFORMATION: primer PA-4DP

<400> SEQUENCE: 10
ggggaattca tatgaaacgt tttcattatg atcgcaataa c                          41

<210> SEQ ID NO 11
<211> LENGTH: 40
<212> TYPE: DNA
<213> ORGANISM: Artificial
<220> FEATURE:
<223> OTHER INFORMATION: primer PA4DKXho

<400> SEQUENCE: 11
aaaagcttct cgagttatcc tatctcatag ccttttttag                            40

<210> SEQ ID NO 12
<211> LENGTH: 1325
<212> TYPE: DNA
<213> ORGANISM: Artificial
<220> FEATURE:
<223> OTHER INFORMATION: nucleotide segment PA-4D +Stop+Term+APH
```

<400> SEQUENCE: 12

```
catatgaaac gttttcatta tgatcgcaat aacatagcag ttggggcgga tgagtcagta        60
gttaaggagg ctcatagaga agtaattaat tcgtcaacag agggattatt gttaaatatt       120
gataaggata taagaaaaat attatcaggt tatattgtag aaattgaaga tactgaaggg       180
cttaaagaag ttataaatga cagatatgat atgttgaata tttctagttt acggcaagat       240
ggaaaaacat ttatagattt taaaaaatat aatgataaat taccgttata tataagtaat       300
cccaattata aggtaaatgt atatgctgtt actaaagaaa acactattat taatcctagt       360
gagaatgggg atactagtac caacgggatc aagaaaattt taatcttttc taaaaaaggc       420
tatgagatag gataactcga cctaagcggc cgctaatccc acagccgcca gttccgctgg       480
cggcattttg gccgcaaggg gtgttatgag ccatattcaa cgggaaacgt cttgctcgag       540
gccgcgatta aattccaaca tggatgctga tttatatggg tataaatggg ctcgcgataa       600
tgtcgggcaa tcaggtgcga caatctatcg attgtatggg aagcccgatg cgccagagtt       660
gtttctgaaa catggcaaag gtagcgttgc caatgatgtt acagatgaga tggtcagact       720
aaactggctg acggaattta tgcctcttcc gaccatcaag catttttatcc gtactcctga       780 tgatgcatgg ttactcacca ctgcgatccc cggaaaaaca gcattccagg tattagaaga       840
atatcctgat tcaggtgaaa atattgttga tgcgctggca gtgttcctgc gccggttgca       900
ttcgattcct gtttgtaatt gtccttttaa cagcgatcgc gtatttcgtc tcgctcaggc       960
gcaatcacga tgaataacg tttggttga tgcgagtgat tttgatgacg agcgtaatgg      1020
ctggcctgtt gaacaagtct ggaaagaaat gcataaactt ttgccattct caccggattc      1080
agtcgtcact catggtgatt tctcacttga taaccttatt tttgacgagg ggaaattaat      1140
aggttgtatt gatgttggac gagtcggaat cgcagaccga taccaggatc ttgccatcct      1200
atggaactgc ctcggtgagt tttctccttc attacagaaa cggctttttc aaaaatatgg      1260
tattgataat cctgatatga ataaattgca gtttcatttg atgctcgatg agttttctta      1320
agctt                                                                 1325
```

<210> SEQ ID NO 13
<211> LENGTH: 32
<212> TYPE: DNA
<213> ORGANISM: Artificial
<220> FEATURE:
<223> OTHER INFORMATION: primer PA-4DK

<400> SEQUENCE: 13

```
aaaagcttat cctatctcat agccttttt ag                                     32
```

<210> SEQ ID NO 14
<211> LENGTH: 439
<212> TYPE: DNA
<213> ORGANISM: Artificial
<220> FEATURE:
<223> OTHER INFORMATION: nucleotide sequence PA-4D cloned to the vector
      pIGCmT7PA-4D in place after digestion with restriction nucleses
      NdeI and HindIII

<400> SEQUENCE: 14

```
catatgaaac gttttcatta tgatcgcaat aacatagcag ttggggcgga tgagtcagta        60
gttaaggagg ctcatagaga agtaattaat tcgtcaacag agggattatt gttaaatatt       120
gataaggata taagaaaaat attatcaggt tatattgtag aaattgaaga tactgaaggg       180
cttaaagaag ttataaatga cagatatgat atgttgaata tttctagttt acggcaagat       240
```

-continued

```
ggaaaaacat ttatagattt taaaaaatat aatgataaat taccgttata tataagtaat    300
cccaattata aggtaaatgt atatgctgtt actaaagaaa acactattat taatcctagt    360
gagaatgggg atactagtac caacgggatc aagaaaattt taatcttttc taaaaaaggc    420
tatgagatag gataagctt                                                 439
```